(12) United States Patent
Re et al.

(10) Patent No.: US 8,153,870 B2
(45) Date of Patent: Apr. 10, 2012

(54) RICE HYBRID XL745

(75) Inventors: Jose V. Re, Friendswood, TX (US);
Yahia H. Ibrahim, Pearland, TX (US);
Eugenio S. Sarreal, Pearland, TX (US)

(73) Assignee: Ricetec, AG, Alvin, TX (US)

( * ) Notice: Subject to any disclaimer, the term of this patent is extended or adjusted under 35 U.S.C. 154(b) by 640 days.

(21) Appl. No.: 12/251,601

(22) Filed: Oct. 15, 2008

(65) Prior Publication Data

US 2010/0095392 A1    Apr. 15, 2010

(51) Int. Cl.
*A01H 1/00*    (2006.01)
*A01H 1/02*    (2006.01)
*A01H 5/00*    (2006.01)
*A01H 5/10*    (2006.01)
*C12N 5/04*    (2006.01)

(52) U.S. Cl. ............. 800/320.2; 800/260; 800/278; 800/295; 800/298; 800/281; 800/284; 800/279; 800/300; 800/301; 800/302; 800/303; 435/410; 435/468; 435/430.1

(58) Field of Classification Search .............. None
See application file for complete search history.

(56) References Cited

U.S. PATENT DOCUMENTS

| | | | |
|---|---|---|---|
| 5,304,719 A | 4/1994 | Segebart | |
| 5,367,109 A | 11/1994 | Segebart | |
| 5,523,520 A | 6/1996 | Hunsperger et al. | |
| 5,763,755 A | 6/1998 | Carlone | |
| 5,850,009 A | 12/1998 | Kevern | |
| 6,956,154 B2 * | 10/2005 | Xie ............ | 800/320.2 |
| 7,301,083 B2 * | 11/2007 | Sarreal et al. ....... | 800/320.2 |

OTHER PUBLICATIONS

Bennetzen, et al., 1992. Approaches and progress in the molecular cloning of plant disease resistance genes. In Genetic Engineering. 14:99-124.
DeBolle, et al., 1996. Antimicrobial peptides from *Mirabilis jalapa* and *Amaranthus caudatus*: expression, processing, localization and biological activity in transgenic tobacco. Plant Molec. Biol. 31:993-1008.
Eshed, et al., 1996. Less-than-additive epistatic interactions of quantitative trait loci in tomato. Genetics 143:1807-1817.
Kraft, et al., 2000. Linkage disequilibrium and fingerprinting in sugar beet. Theor. Appl. Genet. 101:323-326.
Pang, et al., 1992. Expression of a gene encoding a scorpion insectotoxin peptide in yeast, bacteria and plants. Gene 116:165-172.
Poehlman, J.M. and Sleper, D.A., Breeding Field Crops, $4^{th}$ ed. (1995), Iowa State University Press, p. 473.
Smith, C.W. and Dilday, R.H., Origin, Domestication, and Diversification In Rice: Origin, History, Technology, and Production. (2003), John Wiley & Sons, Inc., pp. 4-6.
Yu, et al., 1997. Importance of epistasis as the genetic basis of heterosis in an elite rice hybrid. Proc. Natl. Acad. Sci. 94:9226-9231.

* cited by examiner

*Primary Examiner* — Medina A Ibrahim
(74) *Attorney, Agent, or Firm* — Jondle & Associates, P.C.

(57) ABSTRACT

A rice hybrid designated XL745 is disclosed. The invention relates to the seeds of rice hybrid XL745, to the plants of rice hybrid XL745 and to methods for producing a rice plant produced by crossing the hybrid XL745 with itself or another rice plant. The invention further relates to hybrid rice seeds and plants produced by crossing the hybrid XL745 with another rice plant. This invention further relates to growing and producing blends of rice seeds comprised of seeds of rice hybrid XL745 with rice seed of one, two, three, four or more of another rice hybrid, rice variety or rice inbred.

23 Claims, No Drawings

RICE HYBRID XL745

BACKGROUND OF THE INVENTION

The present invention relates to a new and distinctive rice hybrid designated XL745. All publications cited in this application are herein incorporated by reference.

Rice is an ancient agricultural crop and is today one of the principal food crops of the world. There are two cultivated species of rice: *Oryza sativa* L., the Asian rice, and *Oryza glaberrima* Steud., the African rice. The Asian species constitutes virtually all of the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is from irrigation or rainfall. Another method of planting by the dry-seeded system is to broadcast the seed by airplane into a flooded field, then promptly drain the water from the field. For the dry-seeded system, when the plants have reached sufficient size (four- to five-leaf stage), a shallow permanent flood of water 5 to 16 cm deep is applied to the field until the rice approaches maturity. Rice is grown on flooded soils to optimize grain yields. Heavy clay soils or silt loam soils with hard pan layers about 30 cm below the surface are typical rice-producing soils because they minimize water losses due to percolation.

In the water-seeded system, rice seed is soaked for 12 to 36 hours to initiate germination, and the seed is broadcast by airplane into a shallow-flooded field. Water may be drained from the field for a short period of time to enhance seedling establishment or the seedlings may be allowed to emerge through the shallow flood. In either case, a shallow flood is maintained until the rice approaches maturity. For both the dry-seeded and water-seeded production systems, the rice is harvested with large combines 2 to 3 weeks after draining.

Rice in the United States is classified into three primary market types by grain size and shape as: long-grain, medium grain and short-grain. Typical U.S. long-grain rice cooks dry and fluffy when steamed or boiled, whereas medium- and short-grain rice cooks moist and sticky. Long-grain cultivars have been traditionally grown in the southern states and generally receive higher market prices.

Although specific breeding objectives vary somewhat in the different regions, increasing yield is a primary objective in all programs. Grain yield of rice is determined by the number of panicles per unit area, the number of fertile florets per panicle, and grain weight per fertile floret. Increases in any or all of these yield components provide a mechanism to obtain higher yields. Heritable variation exists for all of these components, and breeders may directly or indirectly select for increases in any of them.

There are numerous steps in the development of any novel, desirable cultivar. Plant breeding begins with the analysis and definition of problems and weaknesses of the current cultivars, followed by the establishment of program goals, and the definition of specific breeding objectives. The next step is selection of parental lines that possess the traits required to meet the program goals. The goal is to combine in a single cultivar an improved combination of desirable traits from the parental sources. These important traits may include higher yield, resistance to diseases and insects, better stems and roots, tolerance to low temperatures, better agronomic characteristics, and grain quality.

The goal of rice plant breeding is to develop new, unique and superior rice cultivars and hybrids. The breeder initially selects and crosses two or more parental lines, followed by selection among the many new genetic combinations. The breeder can theoretically generate billions of new and different genetic combinations via crossing. The breeder has no direct control at the cellular level; therefore, two breeders will never develop the same line, or even very similar lines, having the same rice traits.

Choice of breeding methods to select for the improved combination of traits depends on the mode of plant reproduction, the heritability of the trait being improved, and the type of cultivar used commercially (e.g., $F_1$ hybrid cultivar, pure-line cultivar, etc.). For highly heritable traits, a choice of superior individual plants evaluated at a single location will be effective, whereas for traits with low heritability, selection should be based on mean values obtained from replicated evaluations of families of related plants. Popular selection methods include pedigree selection, backcross selection, and single seed selection, or a combination of these methods.

Pedigree breeding is used commonly for the improvement of self-pollinating crops such as rice. Two parents which possess favorable, complementary traits are crossed to produce an $F_1$. One or both parents may themselves represent an $F_1$ from a previous cross. Subsequently a segregating population is produced, growing the seeds resulting from selfing one or several $F_1$s if the two parents are pure lines or by directly growing the seed resulting from the initial cross if at least one of the parents is an $F_1$. Selection of the best individuals may begin in the first segregating population or $F_2$; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new parental lines.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, rice breeders commonly harvest one or more seeds from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh panicles with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed.

Descriptions of other breeding methods that are commonly used for different traits and crops can be found in one of several reference books (e.g., Allard, R. W. et al. *Principles of Plant Breeding* (1999); Agrawal, R. L. *Fundamentals of Plant Breeding and Hybrid Seed Production* (1998); Schlegel, R. H. J. *Encyclopedic Dictionary of plant Breeding and Related Subjects* (2003); Fehr, W. R. et al. *Principles of Cultivar Development—Theory and Technique* (1987)).

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three or more years. The best lines are candidates for new commercial cultivars; those still deficient in a few traits may be used as parents to produce new populations for further selection.

These processes, which lead to the final step of marketing and distribution, usually take from 8 to 12 years from the time the first cross is made and may rely on the development of improved breeding lines as precursors. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

Each breeding cycle, the plant breeder selects the germplasm to advance to the next generation. This germplasm is grown under unique and different geographical, climatic and soil conditions, and further selections are then made, throughout the growing season. The cultivars which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same cultivar twice by using the exact same original parents and the same selection techniques. This unpredictability results in the expenditure of large amounts of research monies to develop superior new rice cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Rice, *Oryza sativa* L., is an important and valuable field crop. Thus, a continuing goal of rice breeders is to develop stable, high yielding rice cultivars that are agronomically sound. The reasons for this goal are to maximize the amount of grain produced on the land used and to supply food for both animals and humans. To accomplish this goal, the rice breeder must select and develop rice plants that have the traits that result in superior cultivars.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools and methods which are meant to be exemplary and illustrative, not limiting in scope. In various embodiments, one or more of the above-described problems have been reduced or eliminated, while other embodiments are directed to other improvements.

The present invention relates to a hybrid rice designated XL745, and seeds and plants derived from the hybrid. The invention also relates to hybrid plants and seeds and any further progeny or descendants of the hybrid derived by crossing XL745 as a pollen donor. Thus, any methods using hybrid rice XL745 in backcrosses, hybrid production, crosses to populations, and the like, are part of this invention. All plants which are a progeny of or descend from hybrid rice XL745 are within the scope of this invention. It is an aspect of this invention for hybrid rice XL745 to be used in crosses with other, different, rice plants to produce first generation ($F_1$) rice hybrid seeds and plants with superior characteristics.

In another aspect, the present invention provides for single gene converted plants of the parents of hybrid rice XL745. The single transferred gene may preferably be a dominant or recessive allele. Preferably, the single transferred gene will confer such traits as herbicide resistance, insect resistance, resistance to bacterial, fungal, or viral diseases, male fertility, male sterility, enhanced nutritional quality, and industrial usage. The single gene may be a naturally occurring rice gene or a transgene introduced through genetic engineering techniques.

In another aspect, the present invention provides regenerable cells for use in tissue culture of hybrid rice plant XL745. The tissue culture will preferably be capable of regenerating plants having the physiological and morphological characteristics of the foregoing rice plant, and of regenerating plants having substantially the same genotype as the foregoing rice plant. Preferably, the regenerable cells in such tissue cultures will be embryos, protoplasts, meristematic cells, callus, pollen, cotyledon, leaves, flowers, anthers, roots, pistils, root tips, glumes, seeds, panicles or stems. Still further, the present invention provides rice plants regenerated from the tissue cultures of the invention.

In another aspect, the present invention provides for producing a blend consisting of rice seed of rice hybrid XL745 with rice seed of another rice inbred, rice variety or rice hybrid. The blend may also include a first quantity of seed of rice hybrid XL745 with one, two, three, four, five or more quantities of rice seed of another rice hybrid, rice inbred or rice variety.

In another aspect, the present invention also provides for producing a blend of seed of rice hybrid XL745 with seed of one, two, three, four, five or more of another rice hybrid, rice variety or rice inbred where rice hybrid XL745 is present in proportions from 1% up to 95% of the blend. Another aspect of this invention is planting the blend produced with seeds of rice hybrid XL745 and seeds of one, two three, four, five or more of another rice hybrid, rice variety or rice inbred and obtaining a crop with a mix of plants with rice hybrid XL745 as a component. Further, another aspect of this invention is the harvest of seeds from a planted blend of plants of which rice hybrid XL745 is a component of the blend for the purpose of utilizing such seeds for food, feed, as a raw material in industry or as a seed source for planting.

In addition to the exemplary aspects and embodiments described above, further aspects and embodiments will become apparent by study of the following descriptions.

DEFINITIONS

In the description and tables which follow, a number of terms are used. In order to provide a clear and consistent understanding of the specification and claims, including the scope to be given such terms, the following definitions are provided:

Alkali Spreading Value. A 1-7 index used as predictor of starch gelatinization temperature and established by the extent of disintegration of milled rice kernel in contact with a dilute alkali solution. Standard long grains have a 3 to 5 Alkali Spreading Value.

Allele. Allele is any one of many alternative forms of a gene, all of which relate to one trait or characteristic. In a diploid cell or organism, the two alleles of a given gene occupy corresponding loci on a pair of homologous chromosomes.

Alter. The utilization of up-regulation, down-regulation, or gene silencing.

Amylose. Type of grain starch that affects cooking behavior. As such its measured quantity in rice is used to establish cooking properties of Standard US grain classes, or types. (long, medium and short grain).

Apparent Amylose Percent. The percentage of the endosperm starch of milled rice that is amylose. Standard long grains contain 20 to 23 percent amylose. Rexmont-type long grains contain 24 to 25 percent amylose. Short and medium grains contain 14 to 16 percent amylose. Waxy rice contains zero percent amylose. Amylose values, like most characteristics of rice, will vary over environments. "Apparent" refers to the procedure for determining amylose, which may also involve measuring some long chain amylopectin molecules that bind to some of the amylose molecules. These amylopectin molecules actually act similar to amylose in determining the relative hard or soft cooking characteristics.

Backcrossing. Process of crossing a hybrid progeny to one of the parents, for example, a first generation hybrid F1 with one of the parental genotypes of the F1 hybrid.

Blend. Physically mixing rice seeds of a rice hybrid with seeds of one, two, three, four or more of another rice hybrid, rice variety or rice inbred. A blend of rice seed can, for example, also include a mixture of rice seed of rice hybrid XL745 with rice seeds of one, two, three, four, five or more of another rice hybrid, rice variety or rice inbred. Planting a blend of rice seed is comprised of planting, for example, seeds of rice hybrid XL745 with rice seeds of one, two, three, four, five or more of another rice hybrid, rice inbred or rice variety to produce a crop containing the characteristics of all of the rice seeds and plants in this blend.

Breakdown. The Peak Viscosity minus the Trough Viscosity.

Cell. Cell as used herein includes a plant cell, whether isolated, in tissue culture or incorporated in a plant or plant part.

Chalk. An opaque region of the rice kernel resulting from loose packing of the starch granules. Chalk may occur throughout or in a part of the kernel.

Consistency. The Final Viscosity minus the Trough Viscosity.

Cotyledon. A cotyledon is a type of seed leaf. The cotyledon contains the food storage tissues of the seed.

Days to 50% heading. Number of days from emergence to the day when 50% of all panicles are exerted at least partially through the leaf sheath. A measure of growth duration.

Embryo. The embryo is the small plant contained within a mature seed.

Essentially all the physiological and morphological characteristics. A plant having essentially all the physiological and morphological characteristics of the hybrid or cultivar, except for the characteristics derived from the converted gene.

Final Viscosity. The stickiness of rice flour/water slurry after being heated to 95° C. and uniformly cooled to 50° C. in a standardized instrument, specifically the RAPID VISCO Analyzer. Viscosity at the end of the test also defined as Cool Paste Viscosity. (AACC Method 61-02)

Grain Length (L). Length of a whole rice grain measured in millimeters.

Gelatinization temperature. The temperature at which the consistency of a rice flour-water mixture changes into a jelly. Correlates with the cooking time and texture of a rice product.

Gene Silencing. The interruption or suppression of the expression of a gene at the level of transcription or translation.

Genotype. Refers to the genetic constitution of a cell or organism.

Grain Width (W). Width of a whole rice grain measured in millimeters.

Grain Yield. Weight of grain harvested from a given area. Grain yield could also be determined indirectly by multiplying the number of panicles per area, by the number of grains per panicle, and by grain weight.

Harvest Moisture. The percent of moisture of the grain when harvested.

Length/Width (L/W) Ratio. This ratio is determined by dividing the average length (L) by the average width (W).

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Lodging Percent. Lodging is a subjective measured rating, and is the percentage of plant stems leaning or fallen completely to the ground before harvest.

Mixing. Physically mixing whole seeds of two or more genotypes of rice seed. For example, one of the genotypes of rice seed is rice hybrid XL745 mixed with another one, two, three, four, five or more genotypes of rice seed.

1000 Grain Wt. The weight of 1000 rice grains as measured in grams.

Paste Temperature. The temperature at which a defined flour-water mixture exhibits an initial viscosity increase under a standardized protocol utilizing the RAPID VISCO Analyzer. Paste Temperature is an indication of gelatinization temperature.

Paste Time. The time at which Paste Temperature occurs.

Peak Temperature. The temperature at which Peak Viscosity is attained.

Peak Time. The time at which Peak Viscosity is attained.

Peak Viscosity. The maximum viscosity attained during heating when a standardized protocol utilizing the RAPID VISCO Analyzer is applied to a defined rice flour-water slurry. (AACC Method 61-02).

Percent Identity. Percent identity as used herein refers to the comparison of the homozygous alleles of two rice varieties. Percent identity is determined by comparing a statistically significant number of the homozygous alleles of two developed varieties. For example, a percent identity of 90% between rice variety 1 and rice variety 2 means that the two varieties have the same allele at 90% of their loci.

Percent Similarity. Percent similarity as used herein refers to the comparison of the homozygous alleles of a rice variety with another rice plant, and if the homozygous allele of both rice plants matches at least one of the alleles from the other plant then they are scored as similar. Percent similarity is determined by comparing a statistically significant number of loci and recording the number of loci with similar alleles as a percentage. A percent similarity of 90% between the rice plant of this invention and another plant means that the rice plant of this invention matches at least one of the alleles of the other rice plant at 90% of the loci.

Plant. As used herein, the term "plant" includes reference to an immature or mature whole plant, including a plant from which seed or grain or anthers have been removed. Seed or embryo that will produce the plant is also considered to be the plant.

Plant Height. Plant height in centimeters is taken from soil surface to the tip of the extended panicle at harvest.

Plant Part. As used herein, the term "plant part" (or a rice plant, or a part thereof) includes protoplasts, leaves, stems, roots, root tips, anthers, seed, grain, embryo, pollen, ovules, cotyledon, hypocotyl, glumes, panicles, flower, shoot, tissue, cells, meristematic cells and the like.

Pubescence. This refers to a covering of very fine hairs closely arranged on the leaves, stems and glumes of the rice plant.

Quantitative Trait Loci (QTL). Genetic loci that controls to some degree numerically measurable traits that are usually continuously distributed.

Regeneration. Regeneration refers to the development of a plant from tissue culture.

RVA. RAPID VISCO Analyzer is a widely used laboratory instrument utilized to examine the cooking properties of rice flour (i.e. paste time and thickening ability).

Setback. The Final Viscosity minus Peak Viscosity.

Single Gene Converted (Conversion). Single gene converted (conversion) includes plants developed by a plant breeding technique called backcrossing wherein essentially all of the desired morphological and physiological characteristics of an inbred are recovered, while retaining a single gene transferred into the inbred via crossing and backcrossing. The term can also refer to the introduction of a single gene through genetic engineering techniques known in the art.

Total Milling (also call Milling Yield). The quantity of total milled rice produced in the milling of rough rice to a well-milled degree; it is usually expressed as a percent of rough rice by weight, but when specified, may be expressed as a percent of brown rice.

Trough Time. The time at which Trough Viscosity is attained.

Trough Viscosity. The minimum viscosity that occurs after Peak viscosity when a standardized protocol utilizing the Rapid Visco Analyzer is applied to a defined rice flour-water slurry. (AACC Method 61-02)

Whole Milling (also called Head Rice Milling Yield). The quantity of milled head (¾ to whole kernels) rice produced in the milling of rough rice to a well-milled degree, usually expressed in the United States as a percent of rough rice by weight.

DETAILED DESCRIPTION OF THE INVENTION

Rice hybrid XL745 is a high yielding, very early maturing, photoperiod insensitive, long grain hybrid rice cultivar that is tolerant to the imidazolinone class of herbicides. The hybrid has shown uniformity and stability, as described in the following hybrid description information. It has been produced and tested a sufficient number of years with careful attention to uniformity of plant type. Rice hybrid XL745 has been increased with continued observation for uniformity of the parent lines.

Rice hybrid XL745 has the following morphologic and other characteristics (based primarily on data collected at Alvin, Tex.).

TABLE 1

HYBRID DESCRIPTION INFORMATION

Maturity (Alvin, Texas at 150 kg/ha N):

| | |
|---|---|
| Days to maturity: | 71 days from emergence to 50% heading |
| Maturity Class: | Very early (70-85 days) |

Culm (Degrees from perpendicular after flowering):

| | |
|---|---|
| Angle: | Intermediate |
| Length: | 115 cm (Soil level to top of extended panicle on main stem) |
| Height Class: | Medium |
| Internode Color (After flowering): | Green |
| Strength (Lodging resistance): | Moderately weak (most plants leaning with up to 30% lodging) |

Flag Leaf (After Heading):

| | |
|---|---|
| Length: | 37.5 cm |
| Width: | 1.8 cm |
| Pubescence: | Pubescent |

TABLE 1-continued

HYBRID DESCRIPTION INFORMATION

| | |
|---|---|
| Leaf Angle (After heading): | Intermediate |
| Blade Color: | Green |
| Basal Leaf Sheath Color: | Light Purple |
| Ligule: | |
| Color (Late vegetative state): | White |
| Shape: | Cleft |
| Collar Color (Late vegetative stage): | Green |
| Auricle Color (Late vegetative stage): | Pale green |
| Panicle: | |
| Length: | 25 cm |
| Type: | Intermediate |
| Secondary Branching: | Light |
| Exsertion (near maturity): | 91-99% |
| Axis: | Straight |
| Shattering: | Low (1-5%) |
| Threshability: | Intermediate |
| Grain (Spikelet): | |
| Awns (After full heading): | Absent |
| Apiculus Color (At maturity): | Brown |
| Stigma Color: | Purple |
| Stigma Exsertion (at flowering): | 100% |
| Lemma and Palea Color (At maturity): | Straw |
| Lemma and Palea Pubescence: | Hairs present |
| Spikelet Sterility (At maturity): | Highly Fertile (>90%) |
| Grain (Seed): | |
| Seed Coat Color: | Light Brown |
| Endosperm Type: | Nonglutinous (nonwaxy) |
| Endosperm Translucency: | Clear |
| Endosperm Chalkiness: | Small (percentage of grains with more than 20% of chalkiness) |
| Scent: | Nonscented |
| Shape Class (Length/width ratio): | Long |

| Measurements: | Length (mm) | Width (mm) | L/W Ratio | 1000 Grains (g) |
|---|---|---|---|---|
| Milled | 6.90 | 2.24 | 3.06 | 22.2 |
| Milling Yield (% whole kernel (head) rice to rough rice): | 52.0% | | | |
| Apparent Amylose: | 20.0% | | | |
| Alkali Spreading value: | 3.7 (1.5% KOH Solution) | | | |
| Gelatinization Temperature Type: | Intermediate | | | |

| | |
|---|---|
| Herbicide Resistance: | |
| Imidazolinone: | Tolerant |
| Disease Resistance: | |
| Rice Blast (*Pyricularia oryzae*): | Overall Resistance = Moderately Resistant |
| Straight Head: | Moderately Susceptible |
| Sheath Blight (*Rhizoctonia solani*): | Moderately Susceptible |

This invention is also directed to methods for producing a rice plant by crossing a first parent rice plant with a second parent rice plant, wherein the first or second rice plant is a rice plant from hybrid rice XL745. Further, both first and second parent rice plants may be from the hybrid rice XL745. Therefore, any methods using hybrid rice XL745 are part of this invention: selfing, backcrosses, hybrid breeding, and crosses to populations. Any plants produced using hybrid rice XL745 as a parent are within the scope of this invention.

Still further, this invention also is directed to methods for producing a hybrid rice XL745-derived rice plant by crossing rice hybrid XL745 with a second rice plant and growing the progeny seed, and repeating the crossing and growing steps with rice hybrid XL745-derived plant from 0 to 7 times. Thus, any such methods using the rice hybrid XL745 are part of this invention: selfing, backcrosses, hybrid production, crosses to populations, and the like. All plants produced using rice hybrid XL745 as a parent are within the scope of this invention, including plants derived from rice hybrid XL745.

It should be understood that the parents of hybrid rice XL745 can, through routine manipulation of cytoplasmic or other factors, be produced in a male-sterile form. Such embodiments are also contemplated within the scope of the present claims.

FURTHER EMBODIMENTS OF THE INVENTION

The advent of new molecular biological techniques has allowed the isolation and characterization of genetic elements with specific functions such as encoding specific protein products. Scientists in the field of plant biology developed a strong interest in engineering the genome of plants to contain and express foreign genetic elements, or additional, or modified versions of native or endogenous in order to alter the traits of a plant in a specific manner. Any DNA sequences whether from a different species or from the same species which are inserted into the genome via transformation are referred to herein collectively as "transgenes". In some embodiments of the invention, a transgenic variant of rice hybrid XL745 may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years, several methods for producing transgenic plants have been developed, and the present invention, in particular embodiments, also relates to transformed versions of the parents of the claimed hybrid.

Culture for expressing desired structural genes and cultured cells are known in the art. Also as known in the art, rice is transformable and regenerable such that whole plants containing and expressing desired genes under regulatory control may be obtained. General descriptions of plant expression vectors and reporter genes and transformation protocols can be found in Gruber, et al., "Vectors for Plant Transformation", in *Methods in Plant Molecular Biology & Biotechnology*, Glich, et al., (Eds. pp. 89-119, CRC Press, 1993). Moreover GUS expression vectors and GUS gene cassettes are available from Clone Tech Laboratories, Inc., Palo Alto, Calif. while luciferase expression vectors and luciferase gene cassettes are available from ProMega Corp. (Madison, Wis.). General methods of culturing plant tissues are provided for example by Maki, et al., "Procedures for Introducing Foreign DNA into Plants" in *Methods in Plant Molecular Biology & Biotechnology*, Glich, et al., (Eds. pp. 67-88 CRC Press, 1993); and by Phillips, et al., "Cell-Tissue Culture and In-Vitro Manipulation" in Corn & Corn Improvement, 3rd Edition; Sprague, et al., (Eds. pp. 345-387) American Society of Agronomy Inc., 1988. Methods of introducing expression vectors into plant tissue include the direct infection or co-cultivation of plant cells with *Agrobacterium tumefaciens*, Horsch et al., Science, 227:1229 (1985). Descriptions of *Agrobacterium* vector systems and methods for *Agrobacterium*-mediated gene transfer provided by Gruber, et al., supra.

One embodiment of the invention is a process for producing rice hybrid XL745 further comprising a desired trait, said process comprising transforming a rice hybrid plant of XL745 with a transgene that confers a desired trait. Another embodiment is the product produced by this process. In one embodiment the desired trait may be one or more of herbicide resistance, insect resistance, disease resistance, decreased phytate, or modified fatty acid or carbohydrate metabolism. The specific gene may be any known in the art or listed herein, including; a polynucleotide conferring resistance to imidazolinone, sulfonylurea, glyphosate, glufosinate, triazine, benzonitrile, cyclohexanedione, phenoxy proprionic acid and L-phosphinothricin; a polynucleotide encoding a *Bacillus*

*thuringiensis* polypeptide, a polynucleotide encoding phytase, FAD-2, FAD-3, galactinol synthase or a raffinose synthetic enzyme.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (*Maydica* 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A genetic trait which has been engineered into the genome of a particular rice plant may then be moved into the genome of another rice plant using traditional breeding techniques that are well known in the plant breeding arts. For example, a backcrossing approach is commonly used to move a transgene from a transformed rice plant into an already developed rice hybrid or variety, and the resulting backcross conversion plant would then comprise the transgene(s).

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed rice plants, using transformation methods as described below to incorporate transgenes into the genetic material of the rice plant(s).

Expression Vectors for Rice Transformation—Marker Genes

Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., *Proc. Natl. Acad. Sci. U.S.A.*, 80:4803 (1983). Another commonly used selectable marker gene is the hygromycin phosphotransferase gene which confers resistance to the antibiotic hygromycin. Vanden Elzen et al., *Plant Mol. Biol.*, 5:299 (1985).

Additional selectable marker genes of bacterial origin that confer resistance to antibiotics include gentamycin acetyl transferase, streptomycin phosphotransferase, and aminoglycoside-3'-adenyl transferase, the bleomycin resistance determinant. Hayford et al., *Plant Physiol.* 86:1216 (1988); Jones et al., *Mol. Gen. Genet.*, 210:86 (1987); Svab et al., *Plant Mol. Biol.* 14:197 (1990); Hille et al., *Plant Mol. Biol.* 7:171 (1986). Other selectable marker genes confer resistance to herbicides such as glyphosate, glufosinate or bromoxynil. Comai et al., *Nature* 317:741-744 (1985), Gordon-Kamm et al., *Plant Cell* 2:603-618 (1990) and Stalker et al., *Science* 242:419-423 (1988).

Other selectable marker genes for plant transformation not of bacterial origin include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

In vivo methods for visualizing GUS activity that do not require destruction of plant tissue are available. Molecular Probes publication 2908, IMAGENE GREEN, p. 1-4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263: 802 (1994). GFP and mutants of GFP may be used as screenable markers.

Expression Vectors for Rice Transformation—Promoters

Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters—An inducible promoter is operably linked to a gene for expression in rice. Optionally, the inducible promoter is operably linked to a nucleotide sequence encoding a signal sequence which is operably linked to a gene for expression in rice. With an inducible promoter the rate of transcription increases in response to an inducing agent.

Any inducible promoter can be used in the instant invention. See Ward et al., *Plant Mol. Biol.* 22:361-366 (1993). Exemplary inducible promoters include, but are not limited to, that from the ACEI system which responds to copper (Meft et al., *PNAS* 90:4567-4571 (1993)); In2 gene from maize which responds to benzenesulfonamide herbicide safeners (Hershey et al., *Mol. Gen Genetics* 227:229-237 (1991) and Gatz et al., *Mol. Gen. Genetics* 243:32-38 (1994)) or Tet repressor from Tn10 (Gatz et al., *Mol. Gen. Genetics* 227: 229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., *Proc. Natl. Acad. Sci. U.S.A.* 88:0421 (1991)).

B. Constitutive Promoters—A constitutive promoter is operably linked to a gene for expression in rice or the constitutive promoter is operably linked to a nucleotide sequence encoding a signal sequence which is operably linked to a gene for expression in rice.

Many different constitutive promoters can be utilized in the instant invention. Exemplary constitutive promoters include, but are not limited to, the promoters from plant viruses such as the 35S promoter from CaMV (Odell et al., *Nature* 313:810-812 (1985)) and the promoters from such genes as rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)) and maize H3 histone (Lepetit et al., *Mol. Gen. Genetics* 231:276-285 (1992) and Atanassova et al., *Plant Journal* 2 (3): 291-300 (1992)).

The ALS promoter, Xba1/NcoI fragment 5' to the *Brassica napus* ALS3 structural gene (or a nucleotide sequence similarity to said Xba1/NcoI fragment), represents a particularly useful constitutive promoter. See PCT application WO 96/30530.

C. Tissue-specific or Tissue-preferred Promoters—A tissue-specific promoter is operably linked to a gene for expression in rice. Optionally, the tissue-specific promoter is operably linked to a nucleotide sequence encoding a signal sequence which is operably linked to a gene for expression in rice. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476-482 (1983) and Sengupta-Gopalan et al., *Proc. Natl. Acad. Sci. U.S.A.* 82:3320-3324 (1985)); a leaf-specific and light-induced promoter such as that from cab or rubisco (Simpson et al., *EMBO J.* 4(11): 2723-2729 (1985) and Timko et al., *Nature* 318:579-582 (1985)); an anther-specific promoter such as that from LAT52 (Twell et al., *Mol. Gen. Genetics* 217:240-245 (1989)); a pollen-specific promoter such as that from Zm13 (Guerrero et al., *Mol. Gen. Genetics* 244:161-168 (1993)) or a microspore-preferred promoter such as that from apg (Twell et al., *Sex. Plant Reprod.* 6:217-224 (1993)).

Signal Sequences for Targeting Proteins to Subcellular Compartments

Transport of a protein produced by transgenes to a subcellular compartment such as the chloroplast, vacuole, peroxisome, glyoxysome, cell wall or mitochondrion or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992); Knox, C., et al., *Plant Mol. Biol.* 9:3-17 (1987); Lerner et al., *Plant Physiol.* 91:124-129 (1989); Fontes et al., *Plant Cell* 3:483-496 (1991); Matsuoka et al., *Proc. Natl. Acad. Sci.* 88:834 (1991); Gould et al., *J. Cell. Biol.* 108:1657 (1989); Creissen et al., *Plant J.* 2:129 (1991); Kalderon, et al., *Cell* 39:499-509 (1984); Steifel, et al., *Plant Cell* 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92-6 (1981).

According to a preferred embodiment, the transgenic plant provided for commercial production of foreign protein is rice. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson in *Methods in Plant Molecular Biology and Biotechnology* CRC Press, Boca Raton 269:284 (1993).

Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Through the transformation of rice, the expression of genes can be altered to enhance disease resistance, insect resistance, herbicide resistance, agronomic quality and other traits. Transformation can also be used to insert DNA sequences which control or help control male-sterility. DNA sequences native to rice as well as non-native DNA sequences can be transformed into rice and used to alter levels of native or non-native proteins. Various promoters, targeting sequences, enhancing sequences, and other DNA sequences can be inserted into the genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, The Maize Handbook ch. 118 (Springer-Verlag 1994) or other genetic elements such as a FRT, Lox or other site specific integration site, antisense technology (see, e.g., Sheehy et al. (1988) *PNAS USA* 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244: 230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman & Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes That Confer Resistance to Pests or Disease and That Encode:

A. Plant disease resistance genes. Plant defenses are often activated by specific interaction between the product of a disease resistance gene (R) in the plant and the product of a corresponding avirulence (Avr) gene in the pathogen. A plant cultivar can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. *tomato* encodes a protein kinase); Mindrinos et al., *Cell* 78:1089 (1994) (*Arabidopsis* RSP2 gene for resistance to *Pseudomonas syringae*); McDowell & Woffenden, (2003) *Trends Biotechnol.* 21(4): 178-83 and Toyoda et al., (2002) *Transgenic Res.* 11 (6):567-82.

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995 and 31998.

C. A lectin. See, for example, the disclosure by Van Damme et al., *Plant Molec. Biol.* 24:25 (1994), who disclose the nucleotide sequences of several *Clivia miniata* mannose-binding lectin genes.

D. A vitamin-binding protein such as avidin. See PCT application US 93/06487. The application teaches the use of avidin and avidin homologues as larvicides against insect pests.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* α-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in *Diploptera puntata*). Chattopadhyay et al. (2004) *Critical Reviews in Microbiology* 30 (1): 33-54 2004; Zjawiony (2004) *J Nat Prod* 67 (2): 300-310; Carlini & Grossi-de-Sa (2002) *Toxicon,* 40 (11): 1515-1539; Ussuf et al. (2001) *Curr Sci.* 80 (7): 847-853; and Vasconcelos & Oliveira (2004) *Toxicon* 44 (4): 385-403. See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper-accumulation of a monoterpene, a sesquiterpene, a steroid, a hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect *Biochem. Molec. Biol.* 23:691 (1993), who teach the nucleotide sequence of a cDNA encoding tobacco hornworm chitinase, and Kawalleck et al., *Plant Molec. Biol.* 21:673 (1993), who provide the nucleotide sequence of the parsley ubi4-2 polyubiquitin gene, U.S. Pat. Nos. 7,145,060, 7,087,810 and 6,563,020

K. A molecule that stimulates signal transduction. For example, see the disclosure by Botella et al., *Plant Molec. Biol.* 24:757 (1994), of nucleotide sequences for mung bean calmodulin cDNA clones, and Griess et al., *Plant Physiol.* 104:1467 (1994), who provide the nucleotide sequence of a maize calmodulin cDNA clone.

L. A hydrophobic moment peptide. See PCT application WO 95/16776 and U.S. Pat. No. 5,580,852 which discloses peptide derivatives of Tachyplesin which inhibit fungal plant pathogens and PCT application WO 95/18855 and U.S. Pat. No. 5,607,914 which teaches synthetic antimicrobial peptides that confer disease resistance, the respective contents of which are hereby incorporated by reference.

M. A membrane permease, a channel former or a channel blocker. For example, see the disclosure of Jaynes et al., *Plant Sci* 89:43 (1993), of heterologous expression of a cecropin-β, lytic peptide analog to render transgenic tobacco plants resistant to *Pseudomonas solanacearum*.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., *Nature* 366:469 (1993), who show that transgenic plants expressing recombinant antibody genes are protected from virus attack.

Q. A developmental-arrestive protein produced in nature by a pathogen or a parasite. Thus, fungal endo-α-1,4-D-polygalacturonases facilitate fungal colonization and plant nutrient release by solubilizing plant cell wall homo-α-1,4-D-galacturonase. See Lamb et al., *Bio/Technology* 10:1436 (1992). The cloning and characterization of a gene which encodes a bean endopolygalacturonase-inhibiting protein is described by Toubart et al., *Plant J.* 2:367 (1992).

R. A developmental-arrestive protein produced in nature by a plant. For example, Logemann et al., *Bio/Technology* 10:305 (1992), have shown that transgenic plants expressing the barley ribosome-inactivating gene have an increased resistance to fungal disease.

S. Genes involved in the Systemic Acquired Resistance (SAR) Response and/or the pathogenesis-related genes. Briggs, S., *Current Biology,* 5(2) (1995); Pieterse & Van Loon (2004) *Curr. Opin. Plant Bio.* 7(4):456-64 and Somssich (2003) *Cell* 113(7):815-6.

T. Antifungal genes. See Cornelissen and Melchers, *Plant Physiol.*, 101:709-712 (1993); Parijs et al., *Planta* 183:258-264 (1991) and Bushnell et al., *Can. J of Plant Path.* 20(2): 137-149 (1998). Also see U.S. Pat. No. 6,875,907.

U. Detoxification genes, such as for fumonisin, beauvericin, moniliformin and zearalenone and their structurally related derivatives. For example, see U.S. Pat. No. 5,792,931.

V. Cystatin and cysteine proteinase inhibitors. See U.S. Pat. No. 7,205,453.

W. Defensin genes. See WO 03/000863 and U.S. Pat. No. 6,911,577.

2. Genes That Confer Resistance to an Herbicide, For Example:

A. An herbicide that inhibits the growing point or meristem, such as an imidazolinone or a sulfonylurea. Exemplary genes in this category code for mutant ALS and AHAS enzyme as described, for example, by Lee et al., *EMBO J.* 7:1241 (1988), and Miki et al., *Theor. Appl. Genet.* 80:449 (1990), respectively.

B. Glyphosate (resistance conferred by mutant 5-enolpyruvlshikimate-3-phosphate synthase (EPSP) and aroA genes, respectively and other phosphono compounds such as glufosinate (phosphinothricin acetyl transferase (PAT) and *Streptomyces hygroscopicus* PAT bar genes), and pyridinoxy or phenoxy propionic acids and cyclohexanediones (ACCase inhibitor-encoding genes). See, for example, U.S. Pat. No. 4,940,835 to Shah, et al., which discloses the nucleotide sequence of a form of EPSP which can confer glyphosate resistance. U.S. Pat. No. 5,627,061 to Barry et al. also describes genes encoding EPSPS enzymes. See also U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and U.S. Pat. No. 5,491,288; and international publications EP1173580; WO 01/66704; EP1173581 and EP1173582, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. No. 10/427,692. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a PAT gene is provided in European application No. 0 242 246 to Leemans et al. DeGreef et al., *Bio/Technology* 7:61 (1989), describe the production of transgenic plants that express chimeric bar genes coding for PAT activity. Exemplary of genes conferring resistance to phenoxy propionic acids and cyclohexanedione, such as sethoxydim and haloxyfop are the Acc1-S1, Acc1-S2 and Acc1-S3 genes described by Marshall et al., *Theor. Appl. Genet.* 83:435 (1992).

C. An herbicide that inhibits photosynthesis, such as a triazine (psbA and gs+ genes) or a benzonitrile (nitrilase gene). Przibilla et al., *Plant Cell* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., *Biochem. J.* 285:173 (1992).

3. Genes That Confer or Contribute to a Value-Added Trait, Such As:

A. Modified fatty acid metabolism, for example, by transforming a plant with an antisense gene of stearyl-ACP desaturase to increase stearic acid content of the plant. See Knultzon et al., *Proc. Natl. Acad. Sci. U.S.A.* 89:2624 (1992).

B. Decreased phytate content, 1) Introduction of a phytase-encoding gene would enhance breakdown of phytate, adding more free phosphate to the transformed plant. For example, see Van Hartingsveldt et al., *Gene* 127:87 (1993), for a disclosure of the nucleotide sequence of an *Aspergillus niger* phytase gene; 2) Up-regulation of a gene that reduces phytate content. In maize, this, for example, could be accomplished by cloning and then re-introducing DNA associated with one or more of the alleles, such as the LPA alleles identified in maize mutants characterized by low levels of phytic acid. See Raboy et al., *Maydica* 35:383 (1990) and/or by altering inositol kinase activity as in international publication numbers WO 02/059324, WO 03/027243, WO 99/05298, WO 2002/059324, WO 98/45448, WO 99/55882, WO 01/04147; U.S. Publication Numbers 2003/0009011, 2003/0079247; and U.S. Pat. Nos. 6,197,561, 6,291,224, 6,391,348.

C. Modified carbohydrate composition effected, for example, by transforming plants with a gene coding for an enzyme that alters the branching pattern of starch or a gene altering thioredoxin such as NTR and/or TRX (See U.S. Pat. No. 6,531,648 which is incorporated by reference for this purpose) and/or a gamma zein knock out or mutant such as cs27 or TUSC27 or en27 (See U.S. Pat. No. 6,858,778 and U.S. Publication Nos. 2005/0160488 and 2005/0204418, which are incorporated by reference for this purpose). See Shiroza et al., *J. Bacteol.* 170:810 (1988) (nucleotide sequence of *Streptococcus mutanns* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* α-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley α-amylase gene), and Fisher et al., *Plant Physiol.* 102:1045 (1993) (maize endosperm starch branching enzyme II), WO 99/10498 (improved digestibility and/or starch extraction through modification of UDP-D-xylose 4-epimerase, Fragile 1 and 2, Ref 1, HCHL, C4H), U.S. Pat. No. 6,232,529 (method of producing high oil seed by modification of starch levels (AGP)). The fatty acid modification genes mentioned above may also be used to affect starch content and/or composition through the interrelationship of the starch and oil pathways.

D. Altering conjugated linolenic or linoleic acid content, such as in international publication number WO 01/12800. Altering LEC1, AGP, Dek1, Superal1, milps, various Ipa genes such as Ipa1, Ipa3, hpt or hggt. For example, see international publication numbers WO 02/42424, WO 98/22604, WO 03/011015, WO 02/057439, WO 03/011015; U.S. Pat. Nos. 6,423,886, 6,197,561, 6,825,397, 7,157,621; U.S. Publication No. 2003/0079247 and Rivera-Madrid, R. et al. *Proc. Natl. Acad. Sci.* 92:5620-5624 (1995).

E. Altered antioxidant content or composition, such as alteration of tocopherol or tocotrienols. For example, see U.S. Pat. Nos. 6,787,683 and 7,154,029 and international publication number WO 00/68393 involving the manipulation of antioxidant levels through alteration of a phytl prenyl transferase (ppt) and international publication number WO 03/082899 through alteration of a homogentisate geranyl geranyl transferase (hggt).

F. Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), international publication number WO 99/40209 (alteration of amino acid compositions in seeds), international publication number WO 99/29882 (methods for altering amino acid content of proteins), U.S. Pat. No. 5,850,016 (alteration of amino acid compositions in seeds), international publication number WO 98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), international publication number WO 98/56935 (plant amino acid biosynthetic enzymes), international publication number WO 98/45458 (engineered seed protein having higher percentage of essential amino acids), international publication number WO 98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), international publication number WO 96/01905 (increased threonine), international publication number WO 95/15392 (increased lysine), U.S. Pat. Nos. 6,930,225, 7,179,955, 6,803,498, U.S. Publication No. 2004/0068767, international publication numbers WO 01/79516 and WO 00/09706 (Ces A: cellulose synthase), U.S. Pat. No. 6,194,638 (hemicellulose), U.S. Pat. Nos. 6,399,859 and 7,098,381 (UDPGdH) and U.S. Pat. No. 6,194,638 (RGP).

4. Genes that Control Male Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

A. A tapetum-specific gene, RTS, a rice anther-specific gene is required for male fertility and its promoter sequence directs tissue-specific gene expression in different plant species. Luo, Hong, et. al. (2006) *Plant Molecular Biology.* 62(3): 397-408(12). Introduction of a deacetylase gene under the control of a tapetum-specific promoter and with the application of the chemical N-Ac-PPT. See international publication number WO 01/29237.

B. Introduction of various stamen-specific promoters. Rice anther-specific promoters which are of particular utility in the production of transgenic male-sterile monocots and plants for restoring their fertility. See U.S. Pat. No. 5,639,948. See also international publications WO 92/13956 and WO 92/13957.

C. Introduction of the barnase and the barstar genes. See Paul et al., (1992) *Plant Mol. Biol.* 19:611-622.

For additional examples of nuclear male and female sterility systems and genes, see also, U.S. Pat. Nos. 5,859,341, 6,297,426, 5,478,369, 5,824,524, 5,850,014 and 6,265,640. See also Hanson, Maureen R., et. al., (2004) "Interactions of Mitochondrial and Nuclear Genes That Affect Male Gametophyte Development" *Plant Cell.* 16:S154-S169, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see Lyznik, et al., Site-Specific Recombination for Genetic Engineering in Plants, *Plant Cell Rep* (2003) 21:925-932 and international publication number WO 99/25821, which are hereby incorporated by reference. Other systems that may be used include the Gin recombinase of phage Mu (Maeser et al., 1991; Vicki Chandler, The Maize Handbook ch. 118 (Springer-Verlag 1994), the Pin recombinase of *E. coli* (Enomoto et al., 1983), and the R/RS system of the pSR1 plasmid (Araki et al., 1992).

6. Genes that Affect Abiotic Stress Resistance.

Genes that affect abiotic stress resistance (including but not limited to flowering, panicle/glume and seed development, enhancement of nitrogen utilization efficiency, altered nitrogen responsiveness, drought resistance or tolerance, cold resistance or tolerance, and salt resistance or tolerance) and increased yield under stress. For example, see: Xiong, Lizhong, et al., (2003) "Disease Resistance and Abiotic Stress Tolerance in Rice Are Inversely Modulated by an Abscisic Acid-inducible Mitogen-Activated Protein Kinase" *The Plant Cell.* 15:745-759, where OsMAPK5 can positively regulate drought, salt, and cold tolerance and negatively modulate PRgene expression and broad-spectrum disease resistance in rice; Chen, Fang, et. al., (2006) "The Rice 14-3-3 Gene Family and its Involvement in Responses to Biotic and Abiotic Stress" *DNA Research* 13(2):53-63, where at least four rice GF14 genes, GF14b, GF14c, GF14e and Gf14f, were differentially regulated by salinity, drought, wounding and abscisic acid; international publication number WO 00/73475 where water use efficiency is altered through alteration of malate; U.S. Pat. Nos. 5,892,009, 5,965,705, 5,929,305, 5,891,859, 6,417,428, 6,664,446, 6,717,034, 6,801,104 and International Publication Nos. WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 98/09521 and WO 99/38977 describing genes, including CBF genes and transcription factors effective in mitigating the negative effects of freezing, high salinity, and drought on plants, as well as conferring other positive effects on plant phenotype; U.S. Publication No. 2004/0148654 and International Publication No. WO 01/36596 where abscisic acid is altered in plants resulting in improved plant phenotype such as increased yield and/or increased tolerance to abiotic stress; International Publication Nos. WO 2000/006341 and WO 04/090143, U.S. Publication No. 2004/0237147 and U.S. Pat. No. 6,992,237 where cytokinin expression is modified resulting in plants with increased stress tolerance, such as drought tolerance, and/or increased yield. Also see International Publication Nos. WO 02/02776, WO 2003/052063, WO 01/64898, JP2002281975 and U.S. Pat. Nos. 6,084,153, 6,177,275 and 6,107,547 (enhancement of nitrogen utilization and altered nitrogen responsiveness). For ethylene alteration, see U.S. Publication Nos. 2004/0128719 and U.S 2003/0166197 and International Publication No. WO 2000/32761. For plant transcription factors or transcriptional regulators of abiotic stress, see e.g. U.S. Publication Nos. 2004/0098764 and 2004/0078852.

Other genes and transcription factors that affect plant growth and agronomic traits such as yield, flowering, plant growth and/or plant structure, can be introduced or introgressed into plants, see e.g. International Publication Nos. WO 97/49811 (LHY), WO 98/56918 (ESD4), WO 97/10339 WO 96/14414 (CON), WO 96/38560, WO 01/21822 (VRN1), WO 00/44918 (VRN2), WO 99/49064 (GI), WO 00/46358 (FRI), WO 97/29123, WO 99/09174 (D8 and Rht) and U.S. Pat. No. 6,573,430 (TFL), U.S. Pat. No. 6,713,663 (FT), U.S. Pat. Nos. 6,794,560, 6,307,126 (GAI) and International Publication Nos. WO 2004/076638 and WO 2004/031349 (transcription factors).

Methods for Rice Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89-119.

A. *Agrobacterium*-mediated Transformation—One method for introducing an expression vector into plants is based on the natural transformation system of *Agrobacterium*. See, for example, Horsch et al., *Science* 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8:238 (1989). See also, U.S. Pat. No. 5,591,616 issued Jan. 7, 1997.

B. Direct Gene Transfer—Despite the fact the host range for *Agrobacterium*-mediated transformation is broad, some major cereal crop species and gymnosperms have generally been recalcitrant to this mode of gene transfer, even though some success has recently been achieved in rice and corn. Hiei et al., *The Plant Journal* 6:271-282 (1994) and U.S. Pat. No. 5,591,616 issued Jan. 7, 1997. Several methods of plant transformation collectively referred to as direct gene transfer have been developed as an alternative to *Agrobacterium*-mediated transformation.

A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559-563 (1988), Sanford, J. C., *Physiol Plant* 7:206 (1990), Klein et al., *Biotechnology* 10:268 (1992). In corn, several target tissues can be bombarded with DNA-coated microprojectiles in order to produce transgenic plants, including, for example, callus (Type I or Type II), immature embryos, and meristematic tissue.

Another method for physical delivery of DNA to plants is sonication of target cells. Zhang et al., *Bio/Technology* 9:996 (1991). Additionally, liposome and spheroplast fusion have been used to introduce expression vectors into plants. Deshayes et al., *EMBO J.*, 4:2731 (1985), Christou et al., *Proc*

*Natl. Acad. Sci. U.S.A.* 84:3962 (1987). Direct uptake of DNA into protoplasts using $CaCl_2$ precipitation, polyvinyl alcohol or poly-L-ornithine has also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495-1505 (1992) and Spencer et al., *Plant Mol. Biol.* 24:51-61 (1994).

Following transformation of rice target tissues, expression of the above-described selectable marker genes allows for preferential selection of transformed cells, tissues and/or plants, using regeneration and selection methods now well known in the art.

Genetic Marker Profile Through SSR and First Generation Progeny

In addition to phenotypic observations, a plant can also be identified by its genotype. The genotype of a plant can be characterized through a genetic marker profile which can identify plants of the same variety or a related variety or be used to determine or validate a pedigree. Genetic marker profiles can be obtained by techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et. al, "An Integrated Genetic Linkage Map of the Soybean Genome" *Crop Science* 39:1464-1490 (1999), and Berry et al., Assessing Probability of Ancestry Using Simple Sequence Repeat Profiles: Applications to Maize Inbred Lines and Soybean Varieties" *Genetics* 165:331-342 (2003), each of which are incorporated by reference herein in their entirety.

Particular markers used for these purposes are not limited to any particular set of markers, but are envisioned to include any type of marker and marker profile which provides a means of distinguishing varieties. One method of comparison is to use only homozygous loci for hybrid rice XL745.

Primers and PCR protocols for assaying these and other markers are widely known in the art. In addition to being used for identification of rice hybrid XL745 and plant parts and plant cells of rice hybrid XL745, the genetic profile may be used to identify a rice plant produced through the use of hybrid rice XL745 or to verify a pedigree for progeny plants produced through the use of hybrid rice XL745. The genetic marker profile is also useful in breeding and developing backcross conversions.

The present invention comprises a rice hybrid plant characterized by molecular and physiological data obtained from the representative sample of said hybrid deposited with the American Type Culture Collection (ATCC). Further provided by the invention is a rice hybrid plant formed by the combination of the disclosed rice hybrid plant or plant cell with another rice plant or cell.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing hybrids or varieties it is preferable if all SSR profiles are performed in the same lab.

Primers used are publicly available and may be found in for example in U.S. Pat. Nos. 7,232,940, 7,217,003, 7,250,556, 7,214,851, 7,195,887 and 7,192,774.

In addition, plants and plant parts substantially benefiting from the use of rice hybrid XL745 in their development, such as rice hybrid XL745 comprising a backcross conversion, transgene, or genetic sterility factor, may be identified by having a molecular marker profile with a high percent identity to rice hybrid XL745. Such a percent identity might be 95%, 96%, 97%, 98%, 99%, 99.5% or 99.9% identical to rice hybrid XL745.

The SSR profile of rice hybrid XL745 also can be used to identify essentially derived varieties and other progeny varieties developed from the use of rice hybrid XL745, as well as cells and other plant parts thereof. Such plants may be developed using the markers identified in international publication number WO 00/31964, U.S. Pat. No. 6,162,967 and U.S. application Ser. No. 09/954,773. Progeny plants and plant parts produced using rice hybrid XL745 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from a rice hybrid or variety, as measured by either percent identity or percent similarity. Such progeny may be further characterized as being within a pedigree distance of rice hybrid XL745, such as within 1, 2, 3, 4 or 5 or fewer cross-pollinations to a rice plant other than rice hybrid XL745 or a plant that has rice hybrid XL745 as a progenitor. Unique molecular profiles may be identified with other molecular tools such as SNPs and RFLPs.

While determining the SSR genetic marker profile of the plants described supra, several unique SSR profiles may also be identified which did not appear in either parent of such rice plant. Such unique SSR profiles may arise during the breeding process from recombination or mutation. A combination of several unique alleles provides a means of identifying a plant variety, an $F_1$ progeny produced from such variety, and progeny produced from such rice plan.

Singe Gene Conversion

The foregoing methods for transformation would typically be used for producing a transgenic hybrid or cultivar. The transgenic hybrid or cultivar could then be crossed, with another (non-transformed or transformed) cultivar, in order to produce a new transgenic rice plant. Alternatively, a genetic trait which has been engineered into a particular rice hybrid or cultivar using the foregoing transformation techniques could be moved into another hybrid or cultivar using traditional backcrossing techniques that are well known in the plant breeding arts. For example, a backcrossing approach could be used to move an engineered trait from a public, non-elite rice plant into an elite rice plant, or from a rice plant containing a foreign gene in its genome into a rice plant which does not contain that gene. As used herein, "crossing" can refer to a simple X by Y cross, or the process of backcrossing, depending on the context.

When the term rice plant is used in the context of the present invention, this also includes any single gene conversions of that rice hybrid or cultivar. The term single gene converted plant as used herein refers to those rice plants which are developed by a plant breeding technique called backcrossing wherein essentially all of the desired morphological and physiological characteristics of a cultivar are recovered in addition to the single gene transferred into the cultivar via the backcrossing technique. Backcrossing methods can be used with the present invention to improve or introduce a characteristic into the cultivar. The term backcrossing as used herein refers to the repeated crossing of a hybrid progeny back to one of the parental rice plants, the recurrent parent, for that cultivar, i.e., backcrossing 1, 2, 3, 4, 5, 6, 7, 8, 9 or more times to the recurrent parent. The parental rice plant which contributes the gene for the desired characteristic is termed the nonrecurrent or donor parent. This terminology refers to the fact that the nonrecurrent parent is used one time in the backcross protocol and therefore does not recur. The parental rice plant to which the gene or genes from the nonrecurrent parent are transferred is known as the recurrent parent as it is used for several rounds in the backcrossing protocol (Jennings, P. R. et al. *Rice Improvement* (1979); Mackill D. On your mark, get, select. *Rice Today*, July-September. pp 28-29 (2004); Fehr, W. R. et al. *Principles of Cultivar Development—Theory and Technique* pp. 261-286 (1987) and Pohelman and Sleper (1994)).

In a typical backcross protocol, the original cultivar of interest (recurrent parent) is crossed to a second cultivar (nonrecurrent parent) that carries the single gene of interest to be transferred. The resulting progeny from this cross are then crossed again to the recurrent parent and the process is repeated until a rice plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original cultivar. To accomplish this, a single gene of the recurrent cultivar is modified or substituted with the desired gene from the nonrecurrent parent, while retaining essentially all of the rest of the desired genetic, and therefore the desired physiological and morphological, constitution of the original cultivar. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new cultivar but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Introduction of a New Trait or Locus into Rice Hybrid XL745

Rice hybrid XL745 represents a new base genetic hybrid into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of Rice Hybrid XL745

A backcross conversion of rice hybrid XL745 occurs when DNA sequences are introduced through backcrossing (Hallauer et al, 1988, "Corn Breeding" *Corn and Corn Improvements*, No. 18, pp. 463-481), with rice hybrid XL745 utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: *Proceedings Symposium of the Analysis of Molecular Data*, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in *Corn and Corn Improvement*, Sprague and Dudley, Third Ed. 1998). Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal or viral), insect resistance and herbicide resistance. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into rice hybrid XL745 is at least 1, 2, 3, 4, or 5 and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of a site specific integration system allows for the integration of multiple genes at the converted loci.

Tissue Culture

Further reproduction of the hybrid can occur by tissue culture and regeneration. Tissue culture of various tissues of rice and regeneration of plants therefrom is well known and widely published. For example, reference may be had to Komatsuda, T. et al., *Crop Sci.* 31:333-337 (1991); Stephens, P. A., et al., *Theor. Appl. Genet.* (1991) 82:633-635; Komatsuda, T. et al., *Plant Cell, Tissue and Organ Culture,* 28:103-113 (1992); Dhir, S. et al., *Plant Cell Reports* (1992) 11:285-289; Pandey, P. et al., Japan J. Breed. 42:1-5 (1992); and Shetty, K., et al., *Plant Science* 81:245-251 (1992); as well as U.S. Pat. No. 5,024,944 issued Jun. 18, 1991 to Collins et al., and U.S. Pat. No. 5,008,200 issued Apr. 16,1991 to Ranch et al. Thus, another aspect of this invention is to provide cells which upon growth and differentiation produce rice plants having the physiological and morphological characteristics of rice hybrid XL745.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, glumes, panicles, leaves, stems, roots, root tips, anthers, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques, the disclosures of which are incorporated herein by reference.

As used herein, the term "plant" includes plant cells, plant protoplasts, plant cells of tissue culture from which rice plants can be regenerated, plant calli, plant clumps, and plant cells that are intact in plants or parts of plants, such as pollen, flowers, embryos, ovules, seeds, panicles, glumes, leaves, stems, pistils, anthers and the like. Thus, another aspect of this invention is to provide for cells which upon growth and differentiation produce a cultivar having essentially all of the physiological and morphological characteristics of XL745.

The present invention contemplates a rice plant regenerated from a tissue culture of the hybrid rice plant of the present invention. As is well known in the art, tissue culture of rice can be used for the in vitro regeneration of a rice plant. Tissue culture of various tissues of rice and regeneration of plants therefrom is well known and widely published. For example, reference may be had to Chu, Q. R., et al., (1999) "Use of bridging parents with high anther culturability to improve plant regeneration and breeding value in rice", *Rice Biotechnology Quarterly* 38:25-26; Chu, Q. R., et al., (1998), "A novel plant regeneration medium for rice anther culture of Southern U.S. crosses", *Rice Biotechnology Quarterly* 35:15-16; Chu, Q. R., et al., (1997), "A novel basal medium for embryogenic callus induction of Southern US crosses", *Rice Biotechnology Quarterly* 32:19-20; and Oono, K., "Broadening the Genetic Variability By Tissue Culture Methods", *Jap. J. Breed.* 33 (Suppl.2), 306-307, illus. 1983. Thus, another aspect of this invention is to provide cells which upon growth and differentiation produce rice plants having the physiological and morphological characteristics of hybrid XL745.

Duncan, et al., *Planta* 165:322-332 (1985) reflects that 97% of the plants cultured that produced callus were capable of plant regeneration. Subsequent experiments with both cultivars and hybrids produced 91% regenerable callus that produced plants. In a further study in 1988, Songstad, et al., *Plant Cell Reports* 7:262-265 (1988), reports several media additions that enhance regenerability of callus of two cultivars. Other published reports also indicated that "non-traditional" tissues are capable of producing somatic embryogenesis and plant regeneration. K. P. Rao et al., *Maize Genetics Cooperation Newsletter,* 60:64-65 (1986), refers to somatic embryogenesis from glume callus cultures and B. V. Conger, et al., *Plant Cell Reports,* 6:345-347 (1987) indicates somatic embryogenesis from the tissue cultures of corn leaf segments. Thus, it is clear from the literature that the state of the art is such that these methods of obtaining plants are routinely used and have a very high rate of success.

Additional Breeding Methods

The utility of rice hybrid XL745 also extends to crosses with other species. Commonly, suitable species will be of the family Poaceae and especially of the species *sativa* and *glaberrima*.

This invention also is directed to methods for producing a rice plant by crossing a first parent rice plant with a second parent rice plant wherein the first or second parent rice plant is a rice plant of the hybrid XL745. Further, both first and second parent rice plants can come from the rice hybrid XL745. Thus, any such methods using the rice hybrid XL745 are part of this invention: selfing, backcrosses, hybrid production, crosses to populations, and the like. All plants produced using rice hybrid XL745 as a parent are within the scope of this invention, including those developed from varieties derived from rice hybrid XL745. Advantageously, the rice hybrid of the present invention could be used in crosses with other, different, rice plants to produce the first generation ($F_1$) rice hybrid seeds and plants with superior characteristics. One or both parents of the hybrid of the invention can also be used for transformation where exogenous genes are introduced and expressed by one or both of the parents of the invention. Genetic variants created either through traditional breeding methods using one or both of the parents of XL745 or through transformation of one or both of the parents of XL745 by any of a number of protocols known to those of skill in the art are intended to be within the scope of this invention.

The following describes breeding methods that may be used with hybrid XL745 or with one or both of the parents of hybrid XL745 in the development of further rice plants. One such embodiment is a method for developing an XL745-derived progeny rice plant in a rice plant breeding program comprising: obtaining the rice plant, or a part thereof, of rice line XL745, utilizing said plant or plant part as a source of breeding material and selecting an XL745 progeny plant with molecular markers in common with XL745 and/or with morphological and/or physiological characteristics selected from the characteristics listed in Tables 1, 2, 3, or 4. The same method may be used with one or both of the parents of XL745. Breeding steps that may be used in the rice plant breeding program include pedigree breeding, back crossing, mutation breeding, and recurrent selection. In conjunction with these steps, techniques such as RFLP-enhanced selection, genetic marker enhanced selection (for example SSR markers) and the making of double haploids may be utilized.

Another method involves producing a population of XL745 progeny rice plants, comprising crossing rice hybrid XL745 with another rice plant, thereby producing a population of rice plants, which, on average, derive 50% of their alleles from rice hybrid XL745. A plant of this population may be selected and repeatedly selfed or sibbed with a rice cultivar resulting from these successive filial generations. One embodiment of this invention is the rice cultivar produced by this method and that has obtained at least 50% of its alleles from hybrid XL745. The same method may be used with one or both of the parents of XL745.

One of ordinary skill in the art of plant breeding would know how to evaluate the traits of two plant varieties to determine if there is no significant difference between the two traits expressed by those varieties. For example, see Fehr and Walt, Principles of Cultivar Development, p 261-286 (1987). Thus the invention includes rice hybrid XL745 progeny rice plants comprising a combination of at least two XL745 traits selected from the group consisting of those listed in Tables 1, 2, 3, and 4 or the XL745 combination of traits listed in the Summary of the Invention, so that said progeny rice plant is not significantly different for said traits than rice hybrid XL745. Using techniques described herein, molecular markers may be used to identify said progeny plant as a XL745 progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

Progeny of rice hybrid XL745 may also be characterized through their filial relationship with rice hybrid XL745, as for example, being within a certain number of breeding crosses of rice hybrid XL745. A breeding cross is a cross made to introduce new genetics into the progeny, and is distinguished from a cross, such as a self or a sib cross, made to select among existing genetic alleles. The lower the number of breeding crosses in the pedigree, the closer the relationship between rice hybrid XL745 and its progeny. For example, progeny produced by the methods described herein may be within 1, 2, 3, 4 or 5 breeding crosses of rice hybrid XL745.

Pedigree Breeding

Pedigree breeding starts with the crossing of two genotypes, such as rice hybrid XL745 and another rice plant having one or more desirable characteristics that is lacking or which complements rice hybrid XL745. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$, etc. After a sufficient amount of inbreeding, successive filial generations will serve to increase seed of the developed variety. Preferably, the developed variety comprises homozygous alleles at about 95% or more of its loci.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, a rice variety may be crossed with another rice variety to produce a first generation progeny plant. The first generation progeny plant may then be backcrossed to one of its parent varieties to create a BC1 or BC2. Progeny are selfed and selected so that the newly developed variety has many of the attributes of the recurrent parent and yet several of the desired attributes of the non-recurrent parent. This approach leverages the value and strengths of the recurrent parent for use in new rice varieties.

Therefore, an embodiment of this invention is a method of making a backcross conversion of rice hybrid XL745, comprising the steps of crossing a plant of rice hybrid XL745 with a donor plant comprising a desired trait, selecting an $F_1$ progeny plant comprising the desired trait, and backcrossing the selected $F_1$ progeny plant to a plant of rice hybrid XL745. This method may further comprise the step of obtaining a molecular marker profile of rice hybrid XL745 and using the molecular marker profile to select for a progeny plant with the desired trait and the molecular marker profile of rice hybrid XL745. In one embodiment the desired trait is a mutant gene or transgene present in the donor parent.

Recurrent Selection and Mass Selection

Recurrent selection is a method used in a plant breeding program to improve a population of plants. Rice hybrid XL745 is suitable for use in a recurrent selection program. The method entails individual plants cross pollinating with each other to form progeny. The progeny are grown and the superior progeny selected by any number of selection methods, which include individual plant, half-sib progeny, full-sib progeny and selfed progeny. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used in conjunction with molecular marker enhanced selection. In mass selection seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Mutation Breeding

Mutation breeding is another method of introducing new traits into rice hybrid XL745. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in "Principles of Cultivar Development" Fehr, 1993 Macmillan Publishing Company. In addition, mutations created in other rice plants may be used to produce a backcross conversion of rice hybrid XL745 that comprises such mutation.

Breeding with Molecular Markers

Molecular markers may be used in plant breeding methods utilizing rice hybrid XL745.

Isozyme Electrophoresis and RFLPs have been widely used to determine genetic composition. See for example, Dinka, S. J., et al. (2007) "Predicting the size of the progeny mapping population required to positionally clone a gene" Genetics. 176(4):2035-54; Gonzalez, C., et al. (2007) "Molecular and pathogenic characterization of new Xanthomonas oryzae strains from West Africa" Mol. Plant Microbe Interact. 20(5):534-546; Jin, H., et al. (2006) "Molecular and cytogenic characterization of an Oryza officinalis-O. sativa chromosome 4 addition line and its progenies" Plant Mol. Biol. 62(4-5):769-777; Pan, G., et al. (2006) "Map-based cloning of a novel rice cytochrome P450 gene CYP81A6 that confers resistance to two different classes of herbicides" Plant Mol. Biol. 61 (6):933-943.; Huang, W., et al. (2007) "RFLP analysis for mitochondrial genome of CMS-rice" Journal of Genetics and Genomics. 33(4):330-338; Yan, C. J., et al. (2007) "Identification and characterization of a major QTL responsible for erect panicle trait in japonica rice (Oryza sativa L.)" Theor. Appl. Genetics. DOI:10.1007/s00122-007-0635-9; and I. K. Vasil (ed.) DNA-based markers in plants. Kluwer Academic Press Dordrecht, the Netherlands.

SSR technology is currently the most efficient and practical marker technology; more marker loci can be routinely used and more alleles per marker locus can be found using SSRs in comparison to RFLPs. Gealy, David, et al. (2005) "Insights into the Parentage of Rice/red Rice Crosses Using SSR Analysis of US Rice Cultivars and Red Rice Populations". Rice Technical Working Group Meeting Proceedings. Abstract p. 179.; Lawson, Mark J., et al. (2006) "Distinct Patterns of SSR Distribution in the Arabidopsis thaliana and rice genomes" Genome Biology. 7:R14; Nagaraju, J., et al., (2002) "Genetic Analysis of Traditional and Evolved Basmati and Non-Basmati Rice Varieties by Using Fluorescence-based ISSR-PCR and SSR Markers" Proc. Nat. Acad. Sci. USA. 99(9):5836-5841; and Lu, Hong, et al. (2005) "Population Structure and Breeding Patterns of 145 US Rice Cultivars Based on SSR Marker Analysis" Crop Science. 45:66-76. Single Nucleotide Polymorphisms may also be used to identify the unique genetic composition of the invention and progeny varieties retaining that unique genetic composition. Various molecular marker techniques may be used in combination to enhance overall resolution.

Rice DNA molecular marker linkage maps have been rapidly constructed and widely implemented in genetic studies such as in Zhu, J. H., et al. (1999) "Toward rice genome scanning by map-based AFLP fingerprinting" Mol. Gene Genetics. 261(1):184-195; Cheng, Z., et al (2001) "Toward a cytological characterization of the rice genome" Genome Research. 11(12):2133-2141; Ahn, S., et al. (1993) "Comparative linkage maps of the rice and maize genomes" Proc. Natl. Acad. Sci. USA. 90(17):7980-7984; and Kao, F. I., et al. (2006) "An integrated map of Oryza sativa L. chromosome 5" Theor. Appl. Genet. 112(5):891-902. Sequences and PCR conditions of SSR Loci in rice as well as the most current genetic map may be found in RiceBLAST and the TIGR Rice Genome Annotation on the world wide web.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses.

Production of Double Haploids

The production of double haploids can also be used for the development of plants with a homozygous phenotype in the breeding program. For example, a rice plant for which rice hybrid XL745 is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892,1989 and U.S. Pat. No. 7,135,615.

Methods for obtaining haploid plants are also disclosed in Kobayashi, M. et al., Journ. of Heredity 71(1):9-14, 1980, Pollacsek, M., Agronomie (Paris) 12(3):247-251, 1992; Cho-Un-Haing et al., Journ. of Plant Biol., 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Thomas, W J K, et al. (2003) "Doubled haploids in breeding" in Doubled Haploid Production in Crop Plants. Maluszynski, M., et al. (Eds.) Dordrecht, The Netherland Kluwer Academic Publishers. pp. 337-349.

Descriptions of other breeding methods that are commonly used for different traits and crops can be found in one of several reference books (e.g., Allard, 1960; Simmonds, 1979; Sneep et al., 1979; Fehr, 1987).

The seed of rice hybrid XL745, the plant produced from the hybrid seed, the hybrid rice plant produced from the crossing of the hybrid, and various parts of the hybrid rice plant and transgenic versions of the foregoing, can be utilized for human food, livestock feed, and as a raw material in industry.

Tables

The following tables present data on the traits and characteristics of rice hybrid XL745 as compared with CL161, a commonly grown CLEARFIELD rice variety in the U.S. The data was collected from multiple locations and repeated trials. In the following tables, probability figures indicate the probability associated with a paired Student's t-Test used to determine whether two samples are likely to have come from the same two underlying populations that have the same mean.

In Table 2, column 2 shows the yield in kilograms per hectare, column 3 shows the plant height in centimeters, column 4 shows the number of days to 50% flowering, column 5 shows the percent lodging, column 6 shows the total milling percent and column 7 shows the whole milling percent. The number of different locations over which the data were collected is shown in row 3. The data compares yield, plant height, maturity, lodging and milling yields of CL161 versus rice hybrid XL745. Data was collected in Alvin, Tex.

As shown in Table 2, rice hybrid XL745 unexpectedly has significantly higher yield, plant height and lodging. Yet, CL161 flowers earlier and has greater whole milling than XL745. Both, the hybrid and the check have similar total milling.

TABLE 2

|  | Yield (kg/ha) | Plant Height (cm) | Days to 50% Flowering | Lodging % | Total Milling % | Whole Milling % |
| --- | --- | --- | --- | --- | --- | --- |
| XL745 | 10,316 | 113 | 78 | 25.3 | 71.5 | 52.3 |
| CL161 | 7,587 | 99 | 85 | 7.9 | 70.8 | 61.7 |
| Locations | 28 | 26 | 26 | 7 | 19 | 19 |
| Difference | 2,729 | 14 | −7 | 17.4 | 0.7 | −9.3 |
| Probability | 0.000 | 0.000 | 0.000 | 0.003 | 0.388 | 0.000 |

In Table 3, column 2 shows the percent amylose, column 3 shows the alkali spreading value, column 4 shows the grain length in millimeters, column 5 shows the grain width in millimeters, column 6 shows the grain length to width ratio and column 7 shows the percent grain chalk. The number of different locations over which the data was collected is shown in row 3. The data compare the basic quality characteristics of rice hybrid XL745 and CL161. Data was collected in Alvin, Tex.

Unexpectedly, rice hybrid XL745 had significantly lower amylose, and alkali spreading value compared to CL161. Yet, CL161 has a lower grain length, width, grain length to width ratio, and chalk percentage when compared to XL745.

TABLE 3

|  | Amylose | ASV | Length | Width | L/W Ratio | Chalk % |
| --- | --- | --- | --- | --- | --- | --- |
| XL745 | 19.1 | 3.7 | 7.08 | 2.20 | 3.22 | 1.3 |
| CL161 | 19.6 | 4.2 | 6.68 | 2.14 | 3.12 | 0.2 |
| Locations | 12 | 13 | 12 | 12 | 12 | 2 |
| Difference | −0.5 | −0.5 | 0.40 | 0.06 | 0.10 | 1.1 |
| Probability | 0.000 | 0.000 | 0.000 | 0.000 | 0.010 | 0.000 |

In Table 4, column 2 shows the peak viscosity, column 3 shows the peak time, column 4 shows the trough, column 5 shows the trough time, column 6 shows the paste temperature in degrees Celsius, column 7 shows the paste time, column 8 shows the final viscosity, column 9 shows the breakdown, column 10 shows the setback and column 11 shows the consistency of the starch. Table 4 compares starch characteristics between rice hybrid XL745 and CL161. Data was collected in Alvin, Tex.

Rice hybrid XL745 has a higher peak viscosity, peak time, trough, trough time, paste time, final viscosity, and breakdown than CL161. Yet the paste temp was the same when compared to both XL745 and CL161. For setback and consistency rice hybrid XL745 has lower values than CL161.

TABLE 4

|  | Peak Viscosity | Peak Time | Trough | Trough Time | Paste Temp (° C.) | Paste Time | Final Viscosity | Breakdown | Setback | Consistency |
| --- | --- | --- | --- | --- | --- | --- | --- | --- | --- | --- |
| XL745 | 242.7 | 5.7 | 137 | 8.3 | 78 | 3.4 | 269.7 | 105.7 | 27.1 | 132.6 |
| CL161 | 195.6 | 5.6 | 105 | 8.2 | 78 | 3.3 | 239.3 | 90.8 | 43.6 | 134.3 |
| Difference | 47.1 | 0.1 | 32 | 0.1 | 0 | 0.1 | 30.4 | 14.9 | −16.5 | −1.7 |

EXAMPLES

The following examples further describe the materials and methods used in carrying out the invention and the subsequent results. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Growing a Blend of Rice Seed of Rice Hybrid XL745 With Another Rice Hybrid, Inbred or Variety Another method of the present invention is producing a blend of rice seeds by planting the rice seed of rice hybrid XL745 with rice seed of one, two, three, four, five or more of another rice variety, rice inbred or rice hybrid. The seed of rice hybrid XL745 is present in a range of about 1% to about 95%. The blend of rice seeds are then grown to produce rice plants. The seeds of rice hybrid XL745 contained in the blend and the seeds of one, two, three, four, five or more of another rice variety, rice inbred or rice hybrid also contained in the blend are grown in the same field and then harvested together.

Example 2

Preparing a Blend of Rice Seed Using Rice Hybrid XL745

Another method of the present invention is producing a blend of rice seed using the rice seed of rice hybrid XL745. The blend consists of providing for a first quantity of rice seed of rice hybrid XL745, providing for a second, third, fourth, fifth or higher quantity of rice seed of another rice variety, rice hybrid or rice inbred and mixing all quantities of rice seed to produce a blend of rice seed containing hybrid rice XL745 in a range of about 1% to about 95% and rice seed of one, two, three, four, five or more of another rice hybrid, rice inbred or rice variety.

Deposit Information

A deposit of the RiceTec, Inc. proprietary Rice Hybrid XL745 disclosed above and recited in the appended claims has been made with the American Type Culture Collection (ATCC), 10801 University Boulevard, Manassas, Va. 20110. The date of deposit was Apr. 16, 2010. The deposit of 2,500 seeds was taken from the same deposit maintained by RiceTec, Inc. since prior to the filing date of this application. All restrictions will be removed upon granting of a patent, and the deposit is intended to meet all of the requirements of 37 C.F.R. §§1.801-1.809. The ATCC Accession Number is PTA-10834. The deposit will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A hybrid rice seed designated XL745, wherein a representative sample of seed of said hybrid rice was deposited under ATCC Accession No. PTA-10834.

2. A rice plant, or a part thereof, produced by growing the seed of claim 1.

3. Pollen or an ovule of the plant of claim 2.

4. A rice plant, or a part thereof, having all of the physiological and morphological characteristics of the rice plant of claim 2.

5. A tissue culture produced from protoplasts or cells from the rice plant of claim 2, wherein said cells or protoplasts of the tissue culture are produced from a plant part selected from the group consisting of leaves, pollen, embryos, cotyledon, hypocotyl, meristematic cells, roots, root tips, pistils, anthers, flowers, stems, glumes and panicles.

6. A protoplast produced from the plant of claim 2.

7. A rice plant regenerated from the tissue culture of claim 5, wherein the plant has all the morphological and physiological characteristics of rice hybrid XL745.

8. A method for producing a rice seed, wherein the method comprises crossing the plant of claim 2 with a different rice plant and harvesting the resultant hybrid rice seed.

9. A method of producing an herbicide resistant rice plant wherein the method comprises transforming the rice plant of claim 2 with a transgene wherein the transgene confers resistance to an herbicide selected from the group consisting of imidazolinone, cyclohexanedione, sulfonylurea, glyphosate, glufosinate, phenoxy proprionic acid, L-phosphinothricin, triazine and benzonitrile.

10. An herbicide resistant rice plant produced by the method of claim 9.

11. A method of producing a pest or insect resistant rice plant wherein the method comprises transforming the rice plant of claim 2 with a transgene that confers insect resistance.

12. A pest or insect resistant rice plant produced by the method of claim 11.

13. The rice plant of claim 12, wherein the transgene encodes a *Bacillus thuringiensis* endotoxin.

14. A method of producing a disease resistant rice plant wherein the method comprises transforming the rice plant of claim 2 with a transgene that confers disease resistance.

15. A disease resistant rice plant produced by the method of claim 14.

16. A method of producing a rice plant with modified fatty acid metabolism or modified carbohydrate metabolism wherein the method comprises transforming the rice plant of claim 2 with a transgene encoding a protein selected from the group consisting of fructosyltransferase, levansucrase, alpha-amylase, invertase and starch branching enzyme or encoding an antisense of stearyl-ACP desaturase.

17. A rice plant having modified fatty acid metabolism or modified carbohydrate metabolism produced by the method of claim 16.

18. A method of growing a blend of rice seed wherein the method comprises:
   a. planting a blend comprising a first quantity of rice seed of claim 1 mixed with a second quantity of rice seed of another rice variety, rice hybrid or rice inbred;
   b. growing said seeds to produce rice plants; and
   c. harvesting seeds from said rice plants.

19. The method of claim 18, wherein said blend is comprised of seeds from a third, fourth or fifth rice variety, rice hybrid or rice inbred.

20. The method of claim 18, wherein said blend is comprised of about 1% to about 95% of rice hybrid XL745 seed.

21. A method of producing a blend of rice seed wherein the method comprises:
   a. providing a first quantity of rice seed of claim 1;
   b. providing a second quantity of rice seed of another rice variety, rice inbred or rice hybrid; and
   c. producing a blend comprised of mixing said first quantity of rice seed with said second quantity of rice seed.

22. The method of claim 21, wherein said blend consists of seeds from a third, fourth or fifth rice variety, rice inbred or rice hybrid.

23. The method of claim 21, wherein said blend is comprised of about 1% to about 95% of rice hybrid XL745 seed.

* * * * *